(12) United States Patent
Malonek et al.

(10) Patent No.: US 6,348,045 B1
(45) Date of Patent: Feb. 19, 2002

(54) CATHETER WITH DISTAL-END ENGAGING MEANS

(75) Inventors: Dov Malonek, Qiriyat Tivon; Nissim Darvish, Haifa, both of (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/351,726

(22) Filed: Jul. 12, 1999

(51) Int. Cl.$^7$ .............................................. A61M 31/00
(52) U.S. Cl. .................... 604/270; 604/103.04
(58) Field of Search .............. 604/103.04, 102.02, 604/102.03, 103.51, 159, 160, 164.13, 173, 270, 103.01; 606/113, 108

(56) References Cited

U.S. PATENT DOCUMENTS

| | | | |
|---|---|---|---|
| 5,209,741 A | 5/1993 | Spaeth | 604/528 X |
| 5,383,853 A | 1/1995 | Jung et al. | 604/103.04 |
| 5,690,642 A | 11/1997 | Osborne et al. | 604/103.04 X |

*Primary Examiner*—Anhtuan T. Nguyen
(74) *Attorney, Agent, or Firm*—Cowan, Leibowitz & Latman, P.C.; William H. Dippert

(57) ABSTRACT

A catheter is disclosed, comprising an elongated body, having a proximal end and a distal end, wherein at the distal end of said catheter a cap is provided, attached to said distal end, said cap provided with passage adapted to receive a guide-wire slidingly passing through it.

Another preferred embodiment of the present invention is a catheter having a distal and proximal ends wherein said catheter is provided with a cap at its distal end said cap provided with a loop attached to it adapted to receive a guide-wire to pass through said loop.

Yet another preferred embodiment of the present invention is a catheter having a distal and proximal ends wherein said catheter is provided with external coating said coating at the distal end of the catheter provided with a cleavage and a perforation substantially opposite the cleavage so as to allow a guide-wire to be passed through the cleavage and be threaded through said perforation.

3 Claims, 3 Drawing Sheets

CATHETER WITH DISTAL-END ENGAGING MEANS

FIELD OF THE INVENTION

The present invention relates to catheterization. More particularly it relates to a catheter suitable for guidance and positioning within the patient's body using the monorail positioning method or similar methods involving the engagement of the distal end of the catheter to a guide-wire and guiding it by advancing the catheter's distal end along the guide-wire.

BACKGROUND OF THE INVENTION

Catheterization is a well-known regular procedure, employed as a part of various medical treatments, such as intravascular catheterization, urinary catheterization, endotracheal catheterization, brain catheterization (shunt), and other types of catheterization.

In particular, cardiac pacemaker implant procedure had become a standard procedure in cardiology in the past few decades. Cardiac pacemaker implant procedure generally includes implanting the body of the pacemaker itself and one or two pacing electrode leads, usually inserted in the right chamber or atrium of the heart, and providing electric stimuli to the cardiac muscle through the electrodes.

Excitable tissue control (ETC) devices are devices which modulate the activity of excitable tissues by application of non-excitatory electrical field signals to the excitable tissue through suitable electrodes in contact with the tissue. For example, ETC devices may be used, inter alia, to increase or decrease the contractility of cardiac muscle in vitro, in vivo and in situ., as disclosed in detail in PCT application PCT/IL97/00012 (International Publication Number WO 97/25098) to Ben-Haim et al., titled "ELECTRICAL MUSCLE CONTROLLER", incorporated herein by reference. Other methods and applications of ETC devices are disclosed in PCT application PCT/IL97/00231 (International Publication Number WO 98/10828) titled "APPARATUS AND METHOD FOR CONTROLLING THE CONTRACTILITY OF MUSCLES" to Ben Haim et al., incorporated herein by reference, PCT application PCT/IL97/00232 (International Publication Number WO 98/10829) titled "DRUG-DEVICE COMBINATION FOR CONTROLLING THE CONTRACTILITY OF MUSCLES" to Ben Haim et al., incorporated herein by reference and PCT application PCT/IL97/00233 (International Publication Number WO 98/10830) titled "FENCING OF CARDIAC MUSCLES" to Ben Haim et al., incorporated herein by reference, PCT application PCT/IL97/00235 (International Publications Number WO 98/10831) to Ben Haim et al., titled "CARDIAC OUTPUT CONTROLLER", incorporated herein by reference.

There also are known sensing electrodes such as the BIPOLAR SENSOR FOR MUSCLE TISSUE ACTION POTENTIAL DURATION ESTIMATION (Mika et al.) disclosed in U.S. patent application Ser. No. 09/280,486, filed Mar. 30, 1999, incorporated herein by reference.

Other catheters such as drug administration catheters, feeding catheters etc also exist.

The above mentioned devices, as well as other electro-cardiac devices employ electrode leads to transfer the electric signal from the electric device to the muscle tissue (in the case of signal providing devices, such as ETC in its active modality, pacemaker etc.) and/or in the opposite direction (such as the ETC in its passive modality, the action potential duration estimation sensor etc.)

Inserting the electrode leads into the desired location is quite an intricate task and a skilful hand is needed to guide the lead through the blood vessels, and especially through the coronary venous system of the patient, to the final destination in the heart. The complexity of this procedure lies in the problem of navigating the lead safely to its desired target position, passing through vascular junctions and bends, successfully using the right exits en route, and entering the desired path.

The problem arises from the physical and mechanical characteristics of the pacing lead: an electrode lead comprises an elongated body with one or more electrodes exposed at the lead's distal end, electrically connected via electric wiring to a connector at the lead's proximal end (designated to be connected to the pacemaker, ETC device or the like). The body of the lead is tubular, and is relatively soft, collapsible, and flexible, to increase its fatigue resistance and durability.

A common method of catheterization of a pacing lead in position inside the heart's atrium or ventricle is to use a stiffening stylet, inserted inside and threaded through a lumen passing through the lead. When fully inserted through the lead, and advanced forward by pushing its proximal end, the distal tip of the stylet presses against the distal end of the lead, thus the pushing force at the proximal end of the stylet is transferred to the distal end of the lead, pulling the rest of the lead, trailed behind, through the desired route and into the atrium. For the lead to reach the ventricle, it is further passed through the valve separating the atrium from the ventricle.

Navigation of the lead is generally monitored using simultaneous "on-line" fluoroscopic imaging, allowing the medical staff performing the catheterization to observe the advancement of the catheter to the desired location.

But if navigating the lead to the atrium or ventricle is an intricate task, navigating a lead into position inside the coronary veins is an even more a complex job. This is due to the fact that while the lead follows a path into the heart's atrium that is relatively a straight one, with no substantial bends en route, in order to position the distal end of the lead inside the coronary veins, it must pass the coronary sinus and follow a multiple of bends along the way. In this case, the use of a stiffening stylet would prove problematic, as it is not suitable for maneuvering the lead around bends, and may also inflict damage to the blood vessel walls.

Several methods for the positioning of electrode leads inside coronary veins were developed and described in the art.

A known method of catheterization introducing a CS (coronary sinus) lead uses a lead pre-shaped to present a bent tip at its distal end, and incorporated with the use of a stiffening stylet. The bent-tip shape allows navigation of the stylet-driven lead around bends and junctions as the surgeon or technician advances the stylet and rotates the stylet to point the bent tip of the lead in the direction of the bend or desired exit. The pushing force applied on the proximal end of the stylet is transferred to the lead's distal end along the stylet body. When the distal end of the lead reaches the atrium, its bent tip is designed to be easily maneuvered into the coronary sinus. Once the lead tip is inside the coronary sinus further pushing of the stylet advances the lead within the coronary sinus to its end, and into the great cardiac vein. See U.S. Pat. No. 5,683,445 (Swoyer), titled MEDICAL ELECTRICAL LEAD, filed Apr. 29, 1996.

Another known method of catheterization is referred to as over-the-wire catheterization. Mainly used in conjunction with mapping catheters, a guide-wire comprises a stiff but relatively flexible axially, long, thin wire. The guide-wire is pushed forward through the vein until the distal tip reaches a junction. The operator of the guide-wire jiggles with it until the tip enters the desired branch, and then resumes pushing the guide-wire forward. Once the guide-wire has reached the desired location, a catheter or a soft lead is threaded over the guide-wire and advanced to its designated location, and then the guide-wire is removed. An example for the over-the-wire guidance method is described in U.S. Pat. No. 5,389,087 (Miraki), titled FULLY EXCHANGEABLE OVER-THE-WIRE CATHETER WITH RIP SEAM AND GATED SIDE PORT, filed Jun. 29, 1992.

Mapping catheters, such as these used in electrophysiology laboratories (see for example U.S. Pat. No. 5,711,298, titled HIGH RESOLUTION INTRAVASCULAR SIGNAL DETECTION to Littmann et al.), have a semi-stiff lead body and thus the pushing force exerted on the proximal end is transmitted along the catheter's body to its distal tip. The tip itself is more flexible than the rest of the body, and the catheterzation method is carried out in a similar manner to the insertion of the guide-wire described herein. The flexible property of the tip and the relative rigidity of the rest of the catheter body are crucial to the successful deployment of the catheter in this method.

Yet another method of catheterization relates to the monorail design of a mapping catheter. Here too a guide-wire is inserted first and positioned in place, and is used to navigate the catheter to its desired location. However, in this method, the catheter is provided with a perforation at its distal end. The perforated distal end of the catheter is threaded over the guide-wire, and pushed forward. As the catheter is advanced the guide-wire determines the direction of motion, and guides the catheter, its body passing along side the guide-wire, to its targeted position. Obviously, the catheter needs to possess some stiffness in order to be able to transfer the pushing force exerted on its proximal end along its body to the distal end.

An advantage of the monorail introduction method is the possibility of deploying lumen-free catheters, which therefore may be constructed to have smaller diameter, a feature that governs the extent to which a catheter can be inserted in vary narrow passages, such as the coronary venules.

Another advantage of the monorail introduction method is the abolishment of the need for a lengthy residual guide-wire outside the body of the patient, which in the case of the over-the-wire method has to be at least as long as the overall length of the catheter. In the monorail guiding and positioning method of deployment only a short portion of the guide-wire needs to protrude from the patient's body, and as a result it minimizes the risk of the catheter dropping on the floor during handling by the medical staff while attempting to mount it over the guide-wire prior to its insertion into the patient's body. The monorail method of catheterization requires the use of a relatively stiff catheter body, in order to enable the transfer of force from the proximal end to the distal end of the catheter and advance it to its target position.

Another method of guiding and positioning elongated flexible elements into place within a tortuous body passage was disclosed in U.S. Pat. No. 4,824,435, titled INSTRUMENT GUIDANCE SYSTEM (Giesy et al.), filed May 18, 1987, incorporated herein by reference. The guided elements, provided with annular guides adjacent their distal ends, are slid over a guide-wire extending through the passage. In order to provide column strength to advance the elements a tubular pusher was introduced, slidably received on the guide-wire.

Still another catheterization method is described in U.S. patent application Ser. No. 09/317,589, titled A DEVICE AND METHOD FOR DRAGGING AND POSITIONING OF A MEMBER WITHIN A DUCT IN A BODY (Malonek et al.), filed May 24, 1999, incorporated herein by reference. This method employs pulling mechanism instead of pushing mechanism (as described by Giesy et al.). The later method is suitable in particular (but not solely) for rapid exchange catheterization, where it is an advantage to keep the catheter hooked to the guiding device throughout the operation and leading to its removal.

The last two described method involve an additional guidance tool which pushes or drags the catheter to position. The catheter itself is engaged to the guide-wire at its distal end similarly to the monorail-type catheters, and therefore these introduction methods have similar advantages as the monorail method.

An important advantage of the last two methods is that they facilitates the introduction of soft bodied catheters, possessing no or little stiffness, as the catheter is guided in by applying pushing or pulling force on its distal end.

BRIEF DESCRIPTION OF THE INVENTION

The present invention seeks to provide a catheter adapted for deployment using the monorail guidance and positioning method.

Furthermore an object of the present invention is to provide such catheter design that minimizes the risk of an abrupt inadvertent tearing of the catheter distal tip engaged to the guidewire, and consequent disengagement of the catheter from the guide-wire.

It is therefore provided, in accordance with a preferred embodiment of the present invention, a catheter, said catheter comprising an elongated body, having a proximal end and a distal end, wherein at the distal end of said catheter a cap is provided, attached to said distal end, said cap provided with passage adapted to receive a guide-wire slidingly passing through it.

Furthermore, in accordance with a preferred embodiment of the present invention, the catheter is an electrode lead.

Furthermore, in accordance with a preferred embodiment of the present invention, said cap is hollow and is provided with two aligned bores positioned on the cap's mantle.

Furthermore, in accordance with a preferred embodiment of the present invention, said cap serves as an electrode.

Furthermore, in accordance with a preferred embodiment of the present invention, said passage internal diameter is in the range of 11 to 30 milli-inch.

Furthermore, in accordance with a preferred embodiment of the present invention, said passage is aligned diagonally with respect to the central longitudinal imaginary axis of the catheter.

Furthermore, in accordance with a preferred embodiment of the present invention, the angle defined between said passage and the catheter's imaginary central longitudinal axis is not more than 45°.

Furthermore, in accordance with a preferred embodiment of the present invention, said angle ranges between 5°–20°.

Furthermore, in accordance with a preferred embodiment of the present invention, it is provided a catheter having a distal and proximal ends, wherein said catheter is provided with a cap at its distal end, said cap provided with a loop attached to it adapted to receive a guide-wire to pass through said loop.

Furthermore, in accordance with a preferred embodiment of the present invention, said loop is a looped wire.

Furthermore, in accordance with a preferred embodiment of the present invention, said loop is a tubular member.

Furthermore, in accordance with a preferred embodiment of the present invention, said cap is hollow, having a bore at its distal tip through which a looped wire is threaded, and wherein the looped wire is prevented from disengaging from the cap by means of a little disc, located at the inside of said cap, that is larger in size than the bore, and to which the looped wire is attached to.

Furthermore, in accordance with a preferred embodiment of the present invention, said disc is provided with a duct to allow fluids contained thin the catheter to pass through it and be discharged through bore.

Furthermore, in accordance with a preferred embodiment of the resent invention, said loop inner circumference ranges from 11 to 30 milli-inch.

Furthermore, in accordance with a preferred embodiment of the present invention, it is provided a catheter having a distal and proximal ends, wherein said catheter is provided with external coating, said coating at the distal end of the catheter, provided with a cleavage and a perforation substantially opposite the cleavage so as to allow a guide-wire to be passed through the cleavage and be threaded through said perforation.

Furthermore, in accordance with a preferred embodiment of the present invention, said catheter is an electrode lead.

Finally, in accordance with a preferred embodiment of the present invention, said external coating is made of bio-compatible electrically insulating material.

DETAILED DESCRIPTION OF THE INVENTION AND FIGURES

The catheterization techniques relating to the present invention are the monorail guidance method and the pushing (see Giesy) and pulling (see Malonek) guidance methods. All these methods involve the engagement of the catheter to be positioned within the patient's body at its distal end onto a guide-wire, which is deployed prior to that engagement inside the patient's body passage (be it the vasculature, the urinary system, the digestion system, the respiratory system or any other duct system of a body).

The description of catheter designs suitable for monorail guidance or other similar guiding methods seems to lack details and tends to overlook design and engineering considerations. Basically the catheters disclosed in the prior art are described as merely having a perforation at the distal end, or a loop through which the guide-wire is passed.

It should be noted however that catheters, during the insertion procedure, are subjected to some, if not all, of the following forces: friction forces, pulling forces, pushing forces, bending forces, twisting forces, etc. Some of these forces are present simultaneously, and may be opposite in direction or multi-directional.

The resultant force may therefore prove harmful to the completeness of the catheter. In particular the portion of the catheter most likely to be prone to damage is the distal end and especially the portion of the tip where it is engaged onto the guide-wire. The catheter may disengage from the guide-wire if the distal tip is torn off the catheter, or if the perforation is broken at the rim of the perforation. This may occur if the catheter wall is soft or very thin. In the case of catheters deployed in the vasculature, or other narrow duct systems of the body, the lateral dimension of the catheter is very small (in the order of a few mm and even a single mm), and therefore some form of fortification should be administered to the distal tip of the catheter in order to prevent inadvertent disengagement of the catheter from the guide-wire.

Figure 1:
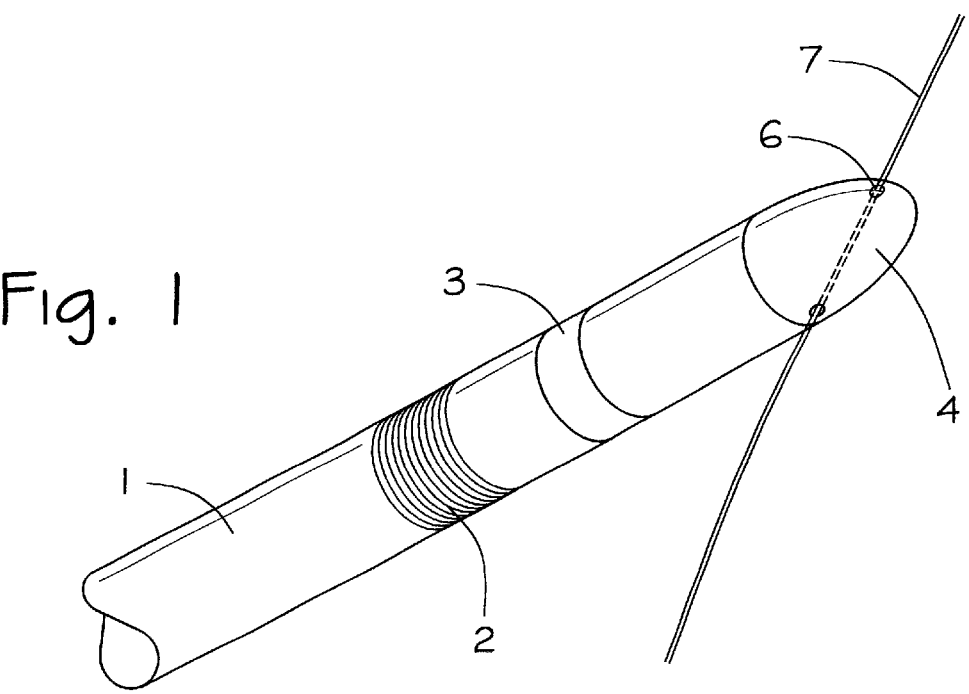
FIG. 1 illustrates a view of a typical embodiment of a catheter suitable for monorail positioning, in accordance with a preferred embodiment of the present invention.

Reference is now made to FIG. 1, illustrating a catheter suitable for monorail guidance, in accordance with a preferred embodiment of the present invention, shown in a partial view. The body of the catheter 1 can in fact be a body of a catheter of any desirable kind (e.g. ETC electrode lead, mapping catheter, pacing electrode lead, etc.). At the distal potion of the catheter—which is this particular embodiment is provided with a coiled electrode 2 and a ring electrode 3—a cap 4 is provided, having a hollow passage extending trough it with two openings, 5, 6. When the catheter is deployed, a guide-wire is first guided through the patient's vasculature (or other duct system of the body), so that the distal end of the guide-wire reached beyond the target position for the distal tip of the catheter. Then, the catheter's distal end cap 4 is slidably mounted over the guide-wire 7, by way of threading the guide-wire 7 through opening 5, the hollow passage within cap 4, and opening 6, and then guiding the catheter along guidewire 7, to the target location within the patient's body. The guiding method employed to guide and position the catheter can be simply applying pushing force at the catheter's proximal end (the so-called "monorail" guiding method), or by pushing or pulling the catheter's distal tip with the help of a guiding aid in a manner as described by Giesy in U.S. Pat. No. 4,824,435, or the method disclosed by Melonek et al. in U.S. patent application Ser. No. 09/317,589.

Figure 2:
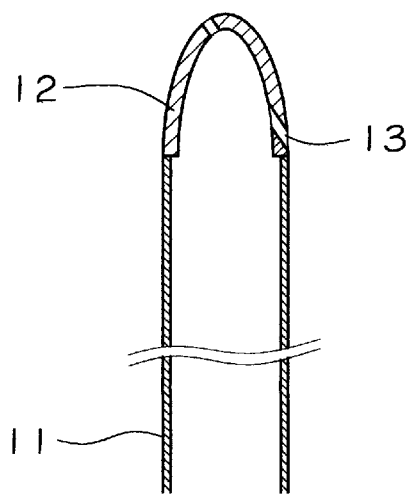
FIG. 2 illustrates a sectional view of the distal end of the catheter provided with a guiding cap.

FIG. 2 illustrates a sectional view of the distal end of a catheter provided with a cap in accordance with a preferred embodiment of the present invention. In this suggested embodiment, cap 12, coupled to the catheter 11, at its distal end, is in fact hollow, and Is provided with two aligned bores 13 positioned on the cap's mantle so as to allow a guide-wire to be threaded through both bores and slidingly pass through the cap.

Figure 3:
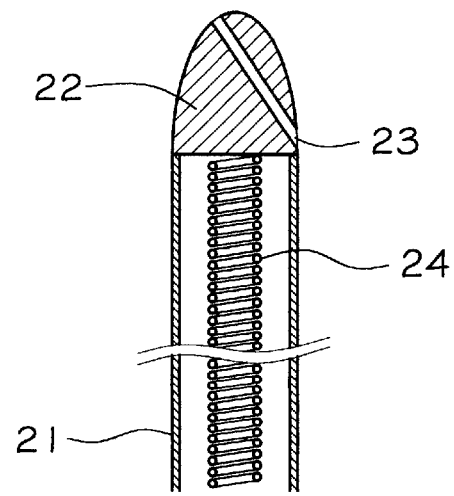
FIG. 3 illustrates a sectional view of the distal end of the catheter provided with a guiding cap of another optional internal design.

FIG. 3 illustrates a sectional view of the distal end of the catheter provided with a guiding cap of another optional internal design. Here the catheter 21 is provided with a cap 22, which unlike the cap shown in FIG. 2 is not hollow. The cap 22 is provided with a bore 23, adapted to receive a guide-wire passing through it. The cap may be adapted to be used also as an electrode, in which case it is provided with electrical wiring 24.

As a typical diameter of a guide-wire for instrument guidance through the vasculature is in the range of 10 to 24 mils (milli-inch), it is recommended, in the case of catheters designated for insertion within the vasculature, to provide the cap with an internal passage adapted to accommodate a guide-wire with inner diameter in the range of 11 to 30 mils.

It is also recommended that the internal passage provided through the cab be constructed diagonally with respect to the central longitudinal imaginary axis of the catheter. The more it is close to that imaginary axis, the more it is convenient to advance the catheter along the guide-wire, as the catheter's body is bound to remain close to the guide-wire, and not protrude too much to impose an obstruction to the safe guiding and advancing of the catheter inside the vasculature. It is therefore recommended that the angle defined locally between the passage through the cap and the catheter's imaginary central longitudinal axis be not more than 45°, and preferably much smaller, in the range of 5°–20°. An angle smaller that 5° would be difficult to obtain as the cap would need to be exceptionally long (the longitudinal dimension of the cap—i.e. its "height"—would then be about 6 times its lateral dimension—i.e. its "width"). An angle greater than 20° may cause the occurrence of leverage between the catheter and the guide-wire that could lead to a kink in the guide-wire, rendering it unfit for guiding and positioning of the catheter.

Figure 4:
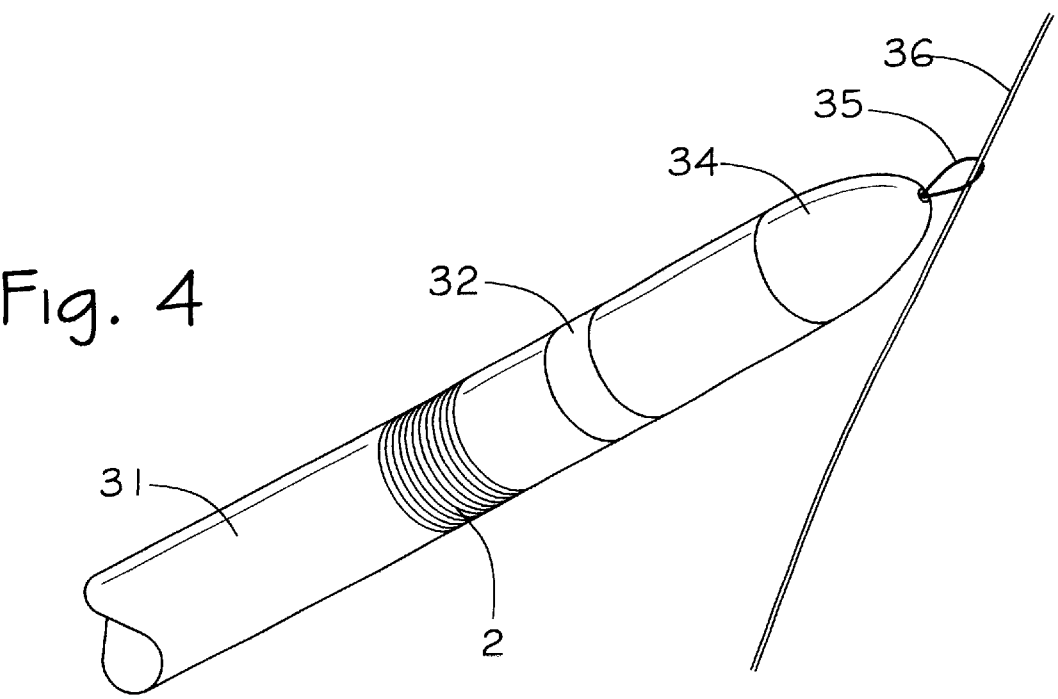
FIG. 4 illustrates a catheter suitable for monorail positioning in accordance with another preferred embodiment of the present invention.

FIG. 4 illustrates a catheter suitable for monorail guidance, in accordance with another preferred embodiment of the present invention. The body of the catheter 31—here an electrode lead with a coiled electrode 32 and a ring electrode 33—is provided, at its distal end, with a cap 34 which has a loop, preferably a looped wire 35 (alternatively a tubular member may also be used) attached to it. The guide-wire 36 is threaded through the looped wire 35, and the catheter Is guided to its target location by employing on of the above mentioned guiding methods. The embodiments presented in FIGS. 4–6 are somewhat more advantageous in terms of guiding convenience over the previous embodiments, as the friction force between the guide-wire and the loop is substantially smaller than the friction exerted between the guide-wire and the internal wall of the cap in the embodiments presented in FIGS. 1–3.

Figure 5:
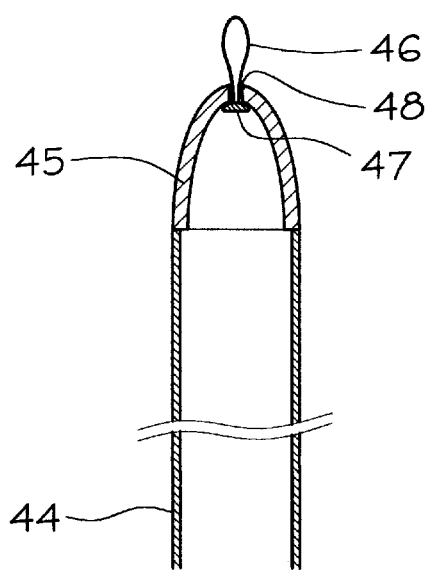
FIG. 5 illustrates a sectional view of the distal end of the catheter in accordance with a preferred embodiment of the present invention.

FIG. 5 illustrates a sectional view of the distal end of a catheter in accordance with a preferred embodiment of the present invention. The catheter 44 is provided at its distal end with a hollow cap 45, having a bore 48 at its distal tip through which a looped wire 46 is threaded. The looped wire 46 is prevented from disengaging from the cap by means of a little disc 47, located at the inside of the cap, that is larger in size than the bore 48, and to which the looped wire is attached to. Disc 47 may optionally be provided with a duct to allow fluids contained within catheter 44 to pass through it and be discharged through bore 48. This may be of particular advantage for a feeding catheter (a hollow catheter which used to convey drugs or feeding substances).

Figure 6:
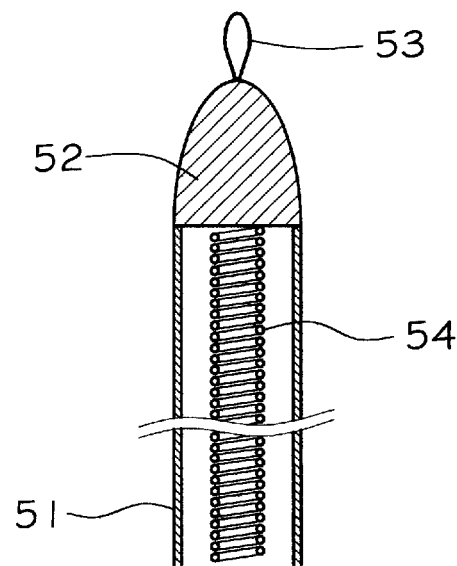
FIG. 6 illustrates a sectional view of an alternative design for the distal end of the catheter shown in FIG. 4.

FIG. 6 illustrates a sectional view of an alternative design for the distal end of the catheter shown in FIG. 4. Here the catheter 51 is provided with a cap which is an electrode 52. The cap 52 is provided with a looped wire 53, coupled to it, adapted to allow passing of a guide-wire through the loop.

Again, as a typical diameter of a guide-wire for instrument guidance through the vasculature is in the range of 10 to 24 mils (milli-inch), it is recommended, in the case of catheters designated for insertion within the vasculature, to provide a looped wire adapted to receive through it a guide-wire, hence the circumference of the wire should be at least in the range of 11 to 30 mils.

For all embodiments shown in FIGS. 1–6 it is recommended to construct the cap from a material possessing relatively high yield strength, at least higher yield strength than the materials from which the catheter body is constructed from. Optionally the cap can be constructed from metal, plastics etc. from friction considerations it is recommended to use material that has a small friction coefficient.

Figure 7:
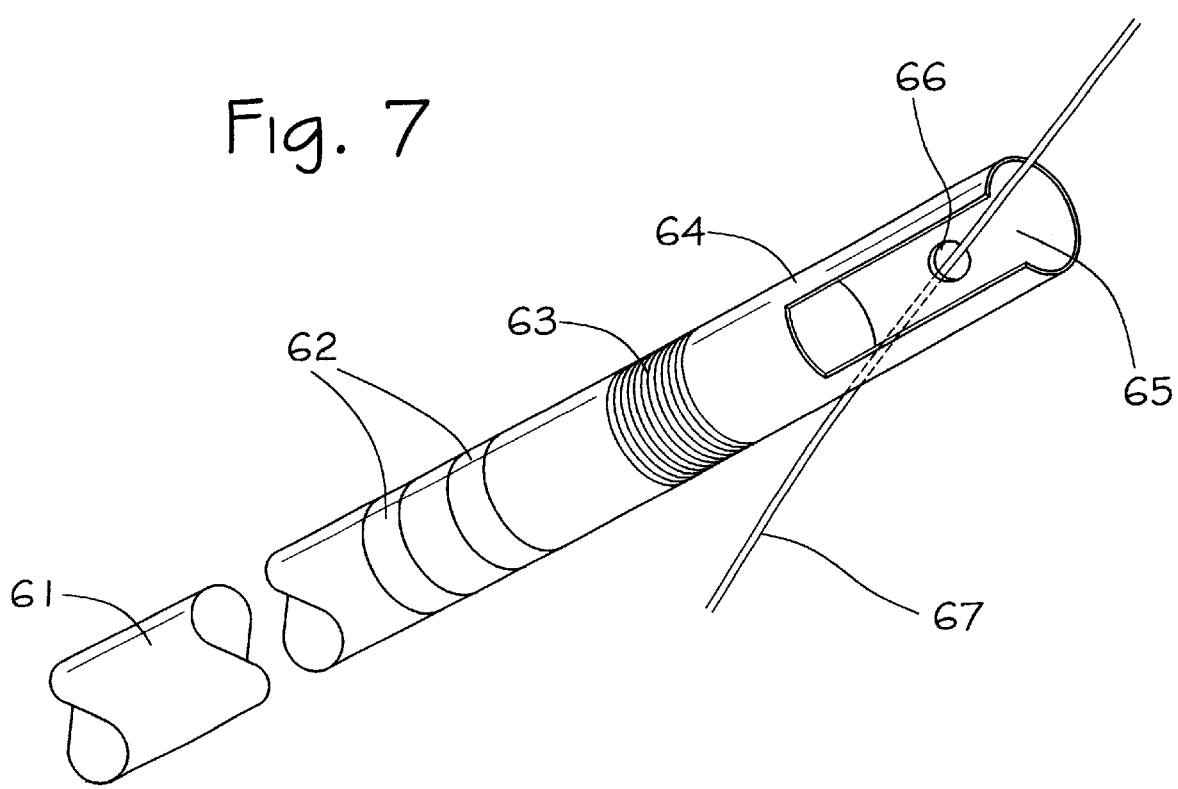
FIG. 7 illustrates a catheter suitable for monorail positioning, in accordance with another preferred embodiment of the present invention.
Figure 8:
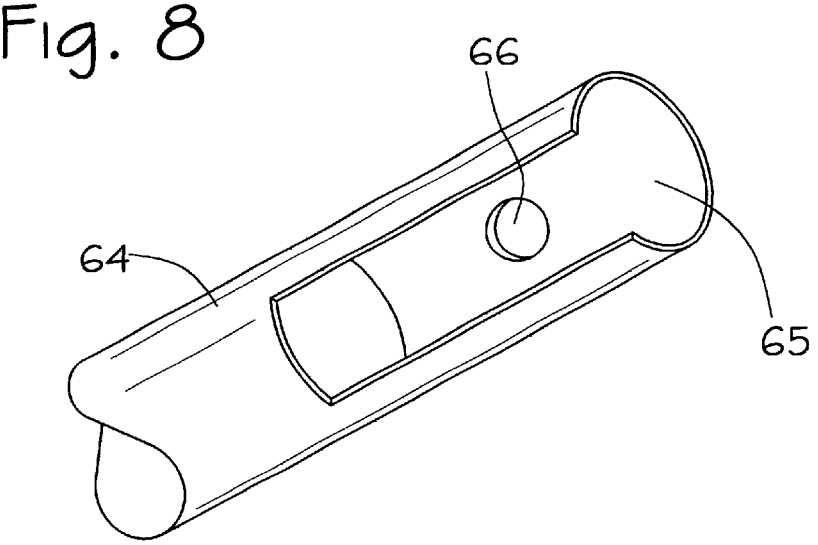
FIG. 8 depicts the distal end of the catheter shown in FIG. 7.

FIG. 7 illustrates a catheter suitable for monorail positioning, in accordance with another preferred embodiment of the present invention. Here the catheter 61 is an electrode lead, provided with two ring electrodes 62 and a coil electrode 63, located at the distal portion of the catheter 61. The catheter is provided with external coating 64—preferably made of bio-compatible electrically insulating material—that extends further than the last electrode (here coil electrode 63) at the distal portion of the catheter to form the distal end of the catheter. The coating 64 of the catheter, at the distal end of the catheter, is provided with a longitudinal cleavage 65, and a perforation 66 substantially opposite the cleavage so as to allow guide-wire 67 to be passed through the cleavage 65 and be threaded through said perforation 66. FIG. 8 depicts the distal end of the catheter shown in FIG. 7, in detail. It should be noted that the diameter of typical cardiac electrode leads (in particular those designed for coronary veins catheterization) may be as small as 1 mm, and it is a demanding task to thread a guide-wire through a perforation located on such a thin catheter. The cleavage provides a convenient way of threading the guide-wire Into the perforation, as the tip of the guide-wire is passed through the cleavage it is practically directed towards the perforation. The cleavage also weakens the radial strength of the coating at the distal end of the catheter, which now more readily submits itself to folding, and thus minimizing the lateral front of the device, bringing the body of the catheter closer to the guide-wire, and hence reducing the active width of the device.

As mentioned earlier, the guiding and positioning of any of the catheters described herein, or any other possible embodiment of a catheter in accordance with a preferred embodiment of the present invention may be performed in any of the methods describe herein, be it with the help of a stylet, or by employing a pulling or pushing aiding tool.

Any embodiment of a catheter in accordance with the present invention (and in particular the catheters disclosed herein) may be used for short-term deployment, or chronic implantation. It may be a hollow catheter, serving to deliver drugs or nutritious substances, or drain liquids (such as urine, blood, mucus, etc.) out of the body.

The catheter of the present invention may be a long catheter, as the ones used in endoscopy, or short, as the ones used in pacing devices. It may be connected to external (out of the body) devices, and also connected to devices implanted inside the body itself.

The disclosed catheter design of the present invention may be incorporated in any type of intravascular catheters, such as mapping catheters (be it electrical mapping, angiography, etc.), pacing electrode catheters, excitable tissue control (ETC) catheters. It may also be incorporated in the design of other types of catheters, such as urinary catheters, gynecological catheters (for example an ovule extraction catheter), brain shunt and others.

It is evident that a major advantage of the present invention is the introduction of very thin cross-section catheters, that can be guided through very narrow ducts and passages of the body, and when a surgical incision is needed for the insertion of the catheter, the catheter of the present invention offers a reduction of the required incision size.

It should be clear that the description of the embodiments and attached Figures set forth in this specification serves only for a better understanding of the invention, without limiting its scope as covered by the following Claims.

It should also be clear that a person in the art, after reading the present specification could make adjustments or amendments to the attached Figures and above described embodiments that would still be covered by the following Claims.

What is claimed is:

1. A catheter having a distal and proximal ends wherein said catheter is provided with external coating said coating at the distal end of the catheter provided with a cleavage and a perforation substantially opposite the cleavage so as to allow a guide-wire to be passed through the cleavage and be threaded through said perforation.

2. The catheter according to claim 1 wherein said catheter is an electrode lead.

3. The catheter according to claim 2 wherein said external coating is made of bio-compatible electrically insulating material.

* * * * *